(12) United States Patent
Makriyannis et al.

(10) Patent No.: US 6,939,977 B2
(45) Date of Patent: Sep. 6, 2005

(54) ANALGESIC AND IMMUNOMODULATORY CANNABINOIDS

(75) Inventors: Alexandros Makriyannis, Mystic, CT (US); Dai Lu, Storrs, CT (US); Atmaram Khanolkar, Coventry, RI (US)

(73) Assignee: The University of Connecticut, Farmington, CT (US)

(*) Notice: Subject to any disclaimer, the term of this patent is extended or adjusted under 35 U.S.C. 154(b) by 0 days.

(21) Appl. No.: 10/309,686

(22) Filed: Dec. 4, 2002

(65) Prior Publication Data
US 2003/0120094 A1 Jun. 26, 2003

Related U.S. Application Data

(63) Continuation of application No. 09/304,720, filed on May 4, 1999, now abandoned.
(60) Provisional application No. 60/084,008, filed on May 4, 1998.

(51) Int. Cl.[7] .............. C07D 311/02; C07D 311/78; C07D 31/80
(52) U.S. Cl. ............ 549/280; 549/388; 549/390; 549/391; 514/455
(58) Field of Search ............... 549/280, 388, 549/390, 391; 514/455

(56) References Cited

U.S. PATENT DOCUMENTS

| 3,041,343 | A | 6/1962 | Jucker et al. |
| 3,465,024 | A | 9/1969 | Brownstein et al. |
| 3,573,327 | A | 3/1971 | Miyano |
| 3,577,458 | A | 5/1971 | Brownstein et al. |
| 3,656,906 | A | 4/1972 | Bullock |

(Continued)

FOREIGN PATENT DOCUMENTS

| EP | 0471609 | 6/1993 |
| EP | 0737671 | 10/1996 |
| EP | 0860168 | 9/2001 |
| GB | 2027021 A | 2/1980 |
| JP | 57098228 | 6/1982 |
| JP | 2304080 | 12/1990 |
| WO | WO 97/00860 | 1/1997 |

(Continued)

OTHER PUBLICATIONS

Abstract from Razdan et al, J. Med. Chem. (1976), 19 (5), 719–21.

(Continued)

Primary Examiner—Rita Desai
(74) Attorney, Agent, or Firm—Alix, Yale & Ristas, LLP

(57) ABSTRACT

Disclosed are novel compounds represented by the following structural formula:

R-X-Y;

and physiologically acceptable salts thereof.

R is a tricyclic core of a cannabinoid or substituted cannabinoid.

X is a covalent bond, —$CH_2$— or —$CHR_1$—, wherein $R_1$ a C1 to C3 substituted or unsubstituted alkyl group.

Y is a heterocyclic ring, a substituted heterocyclic ring, a carbocyclic ring, a substituted carbocyclic ring, a fused bicyclic ring system, a substituted fused bicyclic ring system, a bridged bicyclic ring system, a substituted bridged bicyclic ring system, a bridged tricyclic ring system or a substituted bridged tricyclic ring system.

Also disclosed is a method of stimulating a CB1 and/or CB2 receptor in a subject. The method comprises administering to the subject a therapeutically effective amount of R-X-Y.

14 Claims, 9 Drawing Sheets

U.S. PATENT DOCUMENTS

| | | |
|---|---|---|
| 3,838,131 A | 9/1974 | Gauthier |
| 3,897,306 A | 7/1975 | Vidic |
| 3,928,598 A | 12/1975 | Archer |
| 3,944,673 A | 3/1976 | Archer |
| 3,953,603 A | 4/1976 | Archer |
| 4,054,582 A | 10/1977 | Blanchard et al. |
| 4,087,545 A | 5/1978 | Archer et al. |
| 4,087,546 A | 5/1978 | Archer et al. |
| 4,087,547 A | 5/1978 | Archer et al. |
| 4,088,777 A | 5/1978 | Archer et al. |
| 4,102,902 A | 7/1978 | Archer et al. |
| 4,152,450 A | 5/1979 | Day et al. |
| 4,171,315 A | 10/1979 | Ryan et al. |
| 4,176,233 A | 11/1979 | Archer et al. |
| 4,179,517 A | 12/1979 | Mechoulam et al. ....... 424/283 |
| 4,188,495 A | 2/1980 | Althuis et al. |
| 4,208,351 A | 6/1980 | Archer et al. |
| 4,278,603 A | 7/1981 | Thakkar et al. |
| 4,282,248 A | 8/1981 | Mechoulam et al. |
| 4,382,943 A | 5/1983 | Winter et al. |
| 4,395,560 A | 7/1983 | Ryan |
| 4,497,827 A | 2/1985 | Nelson |
| 4,550,214 A | 10/1985 | Mehta |
| 4,758,597 A | 7/1988 | Martin et al. |
| 4,812,457 A | 3/1989 | Narumiya |
| 4,876,276 A | 10/1989 | Mechoulam et al. ....... 514/454 |
| 4,885,295 A | 12/1989 | Bell et al. |
| 5,053,548 A | 10/1991 | Tanaka et al. |
| 5,068,234 A | 11/1991 | D'Ambra et al. |
| 5,147,876 A | 9/1992 | Mizuchi et al. |
| 5,223,510 A | 6/1993 | Gubin et al. |
| 5,284,867 A | 2/1994 | Kloog et al. ................ 514/454 |
| 5,324,737 A | 6/1994 | D'Ambra et al. |
| 5,434,295 A | 7/1995 | Mechoulam et al. |
| 5,462,960 A | 10/1995 | Barth et al. |
| 5,489,580 A | 2/1996 | Makriyannis et al. |
| 5,521,215 A | 5/1996 | Mechoulam et al. ....... 514/454 |
| 5,532,237 A | 7/1996 | Gallant et al. |
| 5,538,993 A | 7/1996 | Mechoulam et al. ....... 514/454 |
| 5,576,436 A | 11/1996 | McCabe et al. |
| 5,605,906 A | 2/1997 | Lau |
| 5,607,933 A | 3/1997 | D'Ambra et al. |
| 5,618,955 A | 4/1997 | Mechoulam et al. |
| 5,624,941 A | 4/1997 | Barth et al. |
| 5,635,530 A | 6/1997 | Mechoulam et al. ....... 514/454 |
| 5,744,459 A | 4/1998 | Makriyannis et al. |
| 5,747,524 A | 5/1998 | Cullinan et al. |
| 5,804,601 A | 9/1998 | Kato et al. |
| 5,817,651 A | 10/1998 | D'Ambra et al. |
| 5,925,628 A | 7/1999 | Lee et al. |
| 5,925,768 A | 7/1999 | Barth et al. |
| 5,932,610 A | 8/1999 | Shohami et al. |
| 5,948,777 A | 9/1999 | Bender et al. |
| 6,013,648 A | 1/2000 | Rinaldi et al. |
| 6,028,084 A | 2/2000 | Barth et al. |
| 6,096,740 A | 8/2000 | Mechoulam |
| 6,127,399 A | 10/2000 | Yuan |
| 6,166,066 A | 12/2000 | Makriyannis et al. |
| 6,284,788 B1 | 9/2001 | Mittendorf et al. |
| 6,391,909 B1 | 5/2002 | Makriyannis et al. |
| 6,579,900 B2 | 6/2003 | Makriyannis et al. |
| 6,610,737 B1 | 8/2003 | Garzon et al. |
| 2002/0119972 A1 | 8/2002 | Leftheris et al. |
| 2003/0120094 A1 | 6/2003 | Makriyannis et al. |
| 2003/0149082 A1 | 8/2003 | Makriyannis et al. |
| 2004/0077649 A1 | 4/2004 | Makriyannis et al. |
| 2004/0077851 A1 | 4/2004 | Makriyannis et al. |
| 2004/0087590 A1 | 5/2004 | Makriyannis et al. |

FOREIGN PATENT DOCUMENTS

| | | |
|---|---|---|
| WO | WO 99/64389 | 12/1999 |
| WO | WO 00/32200 | 6/2000 |
| WO | WO 01/28329 | 4/2001 |
| WO | WO 01/28497 | 4/2001 |
| WO | WO 01/28498 | 4/2001 |
| WO | WO 01/28557 | 4/2001 |
| WO | WO 01/29007 | 4/2001 |
| WO | WO 01/32169 | 5/2001 |
| WO | WO 01/58869 | 8/2001 |
| WO | WO 03/005960 | 1/2003 |
| WO | WO 03/020217 | 3/2003 |
| WO | WO 03/035005 | 5/2003 |
| WO | WO 03/063758 | 8/2003 |
| WO | WO 03/064359 | 8/2003 |

OTHER PUBLICATIONS

Abstract from Belganokar et al, Indian J. Chem. (1975), 13(4), 336–8.

Rompp Chemie Lexikon (1989), 569–579 (in German).

XP–002226467; Pharmacol. Ther. vol. 74, No. 2, pp. 129–180, 1997 (Pharmacology of Cannabinoid CB1 and CB2 Receptors; Roger G. Pertwee.

Abadji V., Lin S., Taha G., Griffin G., Stevenson L.A., Pertwee R.G., Makriyannis A.; "(R)–Methanadamide: a chiral novel anandamide possessing higher potency and metabolic stability"; J. Med. Chem.; 37(12); 1889–1893; 1994; Coden: JMCMAR; ISSN: 0022–2623; XP002040932.

*1* Alo, B.I.; Kandil, A.; Patil, P. A.; Sharp, M. J.; Siddiqul, M. A.; andd Snieckus, V. Sequential Directed Ortho Metalation–Boronic Acid Cross–Coupling Reactions. A general Regiospecific Route to Oxygenerated Dibenzo[b,d]pyran–6–ones Related to Ellagic Acid, J. Org. Chem. 1991, 56, 3763–3768.

*** Archer et al; "cannabinoids, synthesis approaches to 9–ketocannabinoids."; J. Org. Chem.; vol. 42; No. 13; 2277–2284; (1977).

*1* Arnone M., Maruani J., Chaperon P, et al, Selective inhibition of sucrose and ethanol intake by SR141716, an antagonist of central cannabinoid (CB1) receptors, Psychopharmacal, (1997) 132, 104–106, (abstract only).

*1* Beak, P.; and Brown, R.A., The Tertiary Amide as an Effective Director of Ortho Lithiation, J. Org. Chem. 1982, 47, 34–36.

Beltramo M., Stella N., Calignano A., Lin S. Y., Makriyannis A., Piomelli D; "Functional Role Of High–Affinity Anandamide Transport, as Revealed By Selective Inhibition"; Science; vol. 277; 1094–1097; 1997.

Beltramo M., Stella N., Calignano A., Lin S. Y., Makriyannis A., Piomelli D; "Identification and Functional Role of High Affinity Anandamide Transport"; The Neurosciences Institute (1 page).

Berdyshev EV, Cannabinoid receptors and the regulation of immune response. Chem Phys Lipids. Nov. 2000; 108(1–2): 169–90.

Berglund et al; "Structural requirements for arachidonylethanolamide interaction with CB1 and CB2 cannabinoid receptors: . . . "; Prostanglandins, leukotrienes ands essential fatty acids; 59(2); 111–118; (1998). (abstract only).

Bodnar, V.N., Lozinskii, M.O., Pel'kis, P.S.; "Synthesis fo 2,5–disubstituted 1,3,4–oxadiazoles and 1,4–dihydro–1,2,4,5–tetrazines"; Ukraninskii Khimicheskii Zhurnal (Russian Edition); 48(12); 1308–1311; 1982 (abstract only).

Bracey, M et al, Structural adaptations in a Membrane Enzyme That Terminates Endocannabinoid Signaling. Science 2002; 298(5599): 1793–1796.

*1* Brenneisen R, Pgli A, Elsohly MA, Henn V. Spiess Y: The effect of orally and rectally administered 9—tetrahydrocannabinol on spasticity, a pilot study with 2 patients. Int. J. Clin Pharmacol Ther. (1996) 34:446–452. (abstract only).

*1* *** Brotchie JM: Adjuncts to dopamine replacement a pragmatic approach to reducing the problem of dyskinesia in parkinson's disease. Mov. Disord. (1998) 13:871–876.

*1* Brown et al; "Synthesis and hydroboration of (–)-2-phenylapopinene, Comparison of mono(2-phenylapoisopinocampheyl)borane with its 2-methyl and 2-ethyl analogues for the chiral hydroboration of representative alkenes"; J. Org. Chem.; 55(4); 1217–1223; (1990).

*1* Buckley NE, McCoy Kl, Mpzey E et al, "Immunomodulation by cannabinoids is absent in mice deficient for the cannabinoid CB2 receptor"; Eur. J Pharmacol. (2000) 396:141–149.

*1* Burstein et al; "detection of cannabinoid receptors . . . "; Biochem. Biophys. Res. Commun.; vol. 176(1); 492–497; 1991 (abstract only).

Busch–Peterson et al; "Unsaturated side chain beta–11–hydroxyhexahydrocannabinol analogs"; J. Med. Chem.; 39; 3790–3796; (1996).

*1* Calignano A, La Rana G. Diuffrida A, Piomelli D; "Control of pain Initiation by endogenous cannabinoids"; Nature (1998) 394:277–291. (abstract only).

Calignano A., La Rana G., Beltramo, M., Makriyannis A., Piomelli D; "Potentiation of Anandamide Hypotension by the Transport Zinhibitor, AM404"; Eur. J. Pharmacol.; 1997; 337 R1–R2.

Calignano A., La Rana G., Makriyannis A., Lin. S., Beltramo M., Piomelli D; "Inhibition of Intestinal Motility by Anandamide, an Endogenous Cannabinoid"; Eur. J. Pharmacol.; 1997; 340 R7–R8.

Campbell FA et al; "Are cannabinoids an effective and safe treatment option in the management of pain? A qualitative systematic review"; BMJ. Jul. 7, 2001;323(7303):13–6.

*1* Charalambous A. et al; "5'–azido 8–THC: A Novel Photoaffinity Label for the Cannabinoid Receptor"; J. Med. Chem., 35, 3076–3079 (1992).

*1* Charalambous A. et al; "Pharmacological evaluation of halogenated . . . "; Pharmacol. Biochem. Behav.; vol. 40; No. 3; 509–512; 1991.

*1* Cheng et al; "Relationship Between the Inhibition Constant (Ki) and the concentration of Inhibitor which causes 50% Inhibition (IC50) of an Enzymatic Reaction"; Biochem. Pharmacol., 22, 3099–3102, (1973). (abstract only).

Cherest M., Luscindi X.; "The action of acetyl chloride and of acetic anhydride on the lithium nitronate salt of 2–phenylnitroethane . . . "; Tetrahedron; 42(14); 3825–3840; 1986; in French with English abstract.

Cherest M., Lusinchi X.; "A novel electrophilic N–amidation via electron deficient complexes: action of ferric chloride on N–acetyloxyamides"; Tetrahedron Letters; 30(6); 715–718; 1989.

*1* Colombo G. Agabio R, Diaz G. et al; "Appetite suppression and weight loss after the cannabinoid antagonist SR141716"; Life Sci. (1998) 63–PL13–PL117. (abstract only).

*** Compton D.R. et al.; J. Pharmacol. Exp. Ther.; 260; 201–209; 1992.

*1* Compton et al; "Synthesis and pharmacological evaluation of ether and related analogues of delta8–. delta9– and delta9,11–tetrahydrocannabinol"; J. Med. Chem; vol. 34; No. 11; 3310–3316; 1991.

*1* Consroe P, Musty R, Rein J, Tillery W, Pertwee R; "The perceived effects of smoked cannabis on patents with multiple sclerosis"; Eur. Neurol. (1997) 38–44–48. (abstract only).

Coxon et al; "Derivatives of nopinone"; Aust. J. Chem.; 23; 1069–1071; (1970) (abstract only).

D'Ambra et al; "C–attached aminoalkylindoles: potent cannabinoid mimetics"; Bioorg. & Med. Chem. Lett., 1996, 6(1), 17–22.

*** Damour F.E., Smith D.L.; J. Pharmacol. Exp. Ther.; 72; 74–79; 1941.

Demuynck L. et al; "Rearrangement of Indolo[2,3–a]quinolizindines to derivatives with E–azaaspidospermane skeleton"; Tetrahedron Letters; 30(6) 710–722; 1989; in French with English abstract.

*1* DePetrocellis L, Melck D, Palmisano A. et al; "The endogenous cannabinoid anandamide inhibits human breast cancer cell proliferation"; Proc. Natl. Acad. Sci. USA (Jul. 1998) 95:8375–8380.

Desarnaud F., Cadas H., Piomelli D.; "Anandamide amidohydrolase activity in rat brain microsomes"; J. Biol. Chem.; 270; 6030–6035; (1995).

Deutsch D.G. et al; "Fatty acid sulfonyl fluorides inhibit anandamide metabolism and bind to cannabinoid receptor"; Biochem. Biophys. Res. Commun. 231(1):217–221; 1997; Coden: BBRCA9; ISSN:0006–291X; XP002040933.

Deutsch D.G., Chin S.A.; "Enzymatic synthesis and degradation of anandamide, a cannabinoid receptor agonist", Biochemical Pharmacology; 46(5); 791–796; 1993.

*1* Devane, W.A. et al; "Determination and Characterization of a Cannabinoid Receptor in a Rat Brain"; Mol. Pharmacol., 34, 605–613 (1988). (abstract only).

*1* Di Marzo, V., Melck, D., Bisogno, T., De Petrocellis, L.; "Endocannabinoids: endogenous cannabinoid receptor ligands with neuromodulatory action"; Trends Neurosci. (1998) 21:521–528.

*** Dodd, P.R. et al, A Rapid Method for Preparing Synaptosomes: Comparison with Alternative Procedures, Brain Res., 226, 107–118 (1981).

*1* Dominiami et al; "Synthesis of 5–(tert–Alkyl)resorcinois"; J. Org. Chem. 42(2); 344–346; (1977).

Drake et al, "classical/nonclassical hybrid cannabinoids"; J. Med. Chem.; vol. 41(19): 3596–3608 (1998).

Edery et al; "Activity of novel aminocannabinoids in baboons"; J. Med. Chem.; 27; 1370–1373 (1984).

Fahrenholtz, K. E., Lurie, M. and Kierstead, AR. W.; "The Total Synthesis of dl–Δ9–Tetrahydrocannabinol and Four of Its Isomers"; J. Amer. Chem. Soc. 1967, 89(23), 5934–5941.

Fisera, L., Kovac, J., Lesco, J., Smahovsky, V.; "Furan derivatives. Part CLVI. 1,3–dipolar cycloadditions of heterocycles. V. Reaction of C–acetyl–N–phenylnitrilimine with furan derivatives"; Chemicke Zvesti; 35(1); 93–104 1981 (abstract only).

Galiegue S et al. ; "Expression of central and peripheral cannabinoid receptors in human immune tissues and leukocyte subpopulations"; Eur J Biochem.; Aug. 15, 1995;232(1):54–61. (abstract only).

*1* Gareau, Y.; Dufresne, C.; Gallant, M.; Rochette, C.; Sawyer, N.; Sliptez, D. M.; Tremblay, N.; Weech, P. K.; Metters, K. M.; Labelle, M.; "Structure activity relationsips of tetrahydrocanabinol analogs on human cannabinoid receptors"; Bioorg. Med. Chem. Lett. 1996, 6(2), 189–194.

*1* Gold et al; "A comparison of the discriminative stimulus properties of delta9–tetrahydrocannabinol and CP 55,940 in rats and rhesus monkeys"; J. Pharmacol. Exp. Ther.; vol. 262(2); 479–486; 1992.

*1* *** *Green K. Marijuana smoking vs. cannabinoids for glaucoma therapy. Arch. Ophibalmol. (1998) feb 433–1437.*

*1* Hampson, A.J., Grimaldi M. Axpirod J. Wink D; "Cannabidiol and (–) 9 tetrahydrocannabinol are neuroprotective antioxidants"; Proc. Natl Acad Sci. USA (Jul. 1998) 95: 8268–8273.

*1* Hargreaves, K. et al; "A new sensitive method for measuring thermal nociception in cutaneous hyperalgesia"; Pain; 32; 77–88; (1988) (abstract only).

*1* Herzberg U, Eliav E, Bennett GJ, Kopin IJ; "The analgesic effects of R(+) WIN 55,212–2 mesylate, a high affinity cannabinoid agonist in a rat model of neuropathic pain"; Neurosci. Letts. (1997) 221: 157–160.

Hillard C. J., Edgemond, W. S., Jarrahian W., Campbell, W. B; "Accumulation of N–Arachidonoylethanolamine (Anandamide) into Cerebellar Granule Cells Occurs via Facilitated Diffusion"; Journal of Neurochemistry; 69; 631–638 (1997).

Horrevoets A.J.G et al; "Inactivation of *escherichia coli* outer membrane phospholipase A by the affinity label hexadecanesulfonyl fluoride"; Eur. J. Biochem.; 198; 247–253; 1991.

Horrevoets A.J.G et al; "Inactivation of reconstituted *escherichia coli* outer membrane phospholipase A by membrane–perturbing peptides results in an increased reactivity towards the affinity label hexadecanesulfonyl fluoride"; Eur. J. Biochem.; 198; 255–261; 1991.

Howlett et al; "Azido and isothicyanato substituted aryl pyrazoles bind covalently to the CD1 cannabinoid receptor and impair signal transduction"; Journal of Neurochemistry; vol. 74(5) (2000) 2174–2181; XP001097394.

*1* Howlett et al; "Stereochemical effect of 11–OH–delta 8 tetrahydrocannabinol–dimethylheptyl to inhibit adenylate cyclase and bind to the cannabinoid receptor"; Neuropharmacology; vol. 29(2); 161–165; 1990.

Huffman et al; "3-(1',1'–dimethylbutyl)–deoxy–delta 8THC and related compounds: synthesis of selective ligands for the CB2 receptor"; Bioorganic and Medicinal Chemistry; vol. 7; 2905–2914; (1999).

Huffman et al; "Stereoselective synthesis of the epimeric delta 7–tetrahydocannabinols"; Tetrahedron; vol. 51(4); 1017–1032; (1995).

*1* Huffman et al; "Synthesis of 5', 11 dihydroxy delta 8 tetrahydrocannabinol"; Tetrahedron, vol. 53(39), pp 13295–13306 (1997).

*1* Huffman et al; "Synthesis of both enantiomers of Nabilone from a common intermediate. Enantiodivergent synthesis of cannabinoids"; J. Org. Chem.; 1991, 56, 2081–2086.

Kaminski NE; "Regulation of the cAMP cascade, gene expression and immune function by cannabinoid receptors"; J Neuroimmunol. Mar. 15, 1998 83(1–2):124–32.

Kawase M. et al; "Electrophilic aromatic substitution with N–methoxy–N–acylnitrenium ions generated from N–chloro–N–methoxyamides: synthesis of nitrogen heterocyclic compounds bearing a N–methoxyamide group"; J. Org. Chem.; 54; 3394–3403; 1989.

Khanolkar A., Abadji V., Lin S., Hill W., Taha G., Abouzid K., Meng Z., Fan P., Makriyannis A.; "Head group analogues of arachidonylethanolamide, the endogenous cannabinoid ligand"; J. Med. Chem.; vol. 39(22); 4515–4519; (1996).

Khanolkar et al; "Molecular probes for the cannabinoid receptors"; Chemistry and Physics of Lipids; 108; 37–52; (2000).

Klein T.W. et al, "The cannabinoid system and cytokine network"; Proc Soc Exp Biol Med. Oct. 2000; 225(1):1–8; (abstract only).

Klein TW et al, "Cannabinoid receptors and immunity"; Immunol Today; Aug. 1998; 19(8):373–81.

Koutek B. et al; "Inhibitors of arachidonyl ethanolamide hydrolysis"; J. Biol. Chem.; 269(37); 22937–40; 1994; CODEN: JBCHA3; ISSN: 0021–9258; XP002040931.

Kumar RN, et al; "Pharmacological actions and therapeutic uses of cannabis and cannabinoids"; Anesthesia, 2001, 56: 1059–1068 (abstract only).

Lan, R et al; "Structure activity relationships of pyrazole derivatives as cannabinoid receptor antagonists"; J. Med. Chem.; vol. 42(4); 769–776; (1999).

*1* Lavalle et al; "Efficient conversion of (1R, 5R)–(+)–alpha–pinene to (1S, 5R)–(–)–nopinene"; J. Org. Chem.; vol. 51(8); 1362–1365; (1986).

Lin S., Khanolkar A., Fan P., Goutopolous A., Qin C., Papahadjis D., Makriyannis A.; "Novel Analogues of arachidonylethanolamide (anandamide): affinities for the CB1 and CB2 Cannabinoid Receptors and Metabolic Stability"; J. Med. Chem.; vol. 41; 5353; 1998.

*1* Loev, B., Bender, P. E., Dowalo, F., Macko, E., and Fowler, P.; "Cannabinoids. Structure–Activity Studies Related to 1,2–Dimethylheptyl Derivatives"; J. Med. Chem.; vol. 16(11); 1200–1206; 1973.

Lozinskii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635–2637; 1990 (abstract only).

*1* Ludt, R.E. et al; "A comparison of the synthetic utility of n–butyllithium and lithium diisopropylamide in the metalations of N,N–dialkyltouamides"; J. Org. Chem.; 38(9); 1668–1674 (1973).

Mackie K., Devane W.A., Hille B.; "Anandamide, and endogenous cannabinoid, inhibits calcium currents as a partial agonist in N18 neuroblastoma cells"; Mol. Pharmacol; 44; 498–0503 (1993).

*1* Martin et al; "Behavioral, biochemical, and molecular modeling evaluations of cannabinoid analogs"; Pharmacol. Biochem. Behav.; vol. 40(3); 471–478; 1991.

*1* Martyn CN. Illis LS, Thom J.; "Nabilone in the treatment of multiple sclerosis"; Lancet (1995) vol. 345; pp. 579.

*1* *** *Maurer M, Henn V, Dittrich A, Hoffmann A. Delta–9–tetrahydrocannabinol shows antispastic and analgesic effects in a single case double–blind trial. Eur. Arch. Psychiat. Clin. Neurosci. (1990), Z40:1–4.*

Mechoulam et al; "Stereochemical Requirements for cannabinoid activity"; J. Med. Chem.; 23(10); 1068–1072; (1980).

Mechoulam et al; "Synthesis of the individual, pharmacologically distinct, enantiomers of a tetrahydrocannabinol derivative"; Tetrahedron Asymmetry; 1; 311–314; (1990) (abstract only).

*1* Meltzer et al; "An improved synthesis of cannabinol and cannabiorcol"; Synthesis; 1981:985 (1981).

Melvin et al; "Structure–activity relationships for cannabinoid receptor–binding and analgesic activity: studies of bicyclic cannabinoid analogs"; Mol. Pharmacol.; 44(5); 1008–1015 (1993).

*1* Merck Index; 11th edition; "Tetrahydrocannabinols" compound No. 9142; 1989.

*1* *** Morgan Dr: Therapeutic Uses of Cannabis. Harwood Academic Publishers, Amsterdam. (1997).

Neunhoeffer O., Gottschlich R.; "Acylating activity of O–acylated hydroxylamine derivatives"; Justus Liebigs Ann. Chem.; 736; 100–109; 1970; in German with English abstract.

*1* Novak, J et al; Cannabis, part 27, synthesis of 8–, 10– and 11–oxygenated cannabinoids; J. Chem. Soc. Perkin Trans.; 2867–2871; (1983) (abstract only).

*1* Nye et al; "High affinity cannabinoid binding sites in brain membranes labelled with [H]–5'–trimethylammonium delta8–tetrahydrocannabinol"; J. Pharmacol. Exp. Ther.; vol. 234(3); 784–791; 1985.

*1* Papahatjis et al; "A new ring–forming methodology for the synthesis of conformationally constrained bioactive molecules"; Chemistry Letters, 192; (2001).

*1* Papahatjis et al; "Pharmacophoric requirements for cannabinoid side chains: multiple bond and C1'–substituted delta8–tetrahydrocannabinols"; J. Med. Chem.; 41(7); 1195–1200; (1998).

Pertwee et al; "AM630, a competitive cannabinoid receptor agonist"; Life Sci. 1995, 56(23/24), 1949–1955; XP 000653566.

Pertwee et al; "Pharmacological characterization of three novel cannabinoid receptor agonists in the mouse isolated vas deferens"; Eur. J. Pharmacol. 1995, 284, 241–247; XP–001041044.

*** Pertwee et al; Br. J. Pharmacol.; 105; 980 1992.

Petrov, M.L., Terent'eva, N.A., Potekhin, K.A., Struchkov, Yu. T.; ".alpha.,.beta.–unsaturated thiolates and their analogs in cycloaddition reactions. XVII. Reaction of (2–phenylethynyl)tellurolates with C–ethoxycarbonyl–N–Phenylnitrilimine"; Zhurnal Organicheskoi Khimii; 29(7); 1372–1378; (1993) (abstract only).

*1* *** Pinnegan–Ling D, Musty R.; Marinol and phantom limb pain: a case study. Proc Inv. Cannabinoid Rea. Sec. (1994):53.

Piomelli D., Beltramo M., Glasnapp S., Lin S.Y., Goutopoulos A., Xiw X–Q., Makriyannis A.; "Structural determinants for recognition and translocation by the anandamide transporter"; Proc. Natl. Acad. Sci. USA; 96; 5802–5807; (1999).

*** Porreca F., Mosberg H. I., Hurst R., Hruby V.J., Burks T.F.; "Roles of mu, delta and kappa opiod receptors in spinal and supraspinal mediation of gastrointestinal transit effects and hot–plate analgesia in the mouse"; J. Pharmacol. Exp. Ther.; 230; 341–348; (1994).

*1* Reggio et al; "Characterization of a region of steric interference at the cannabinoid receptor using the active analog approach"; J. Med. Chem. United States; vol. 36(12); 1761–1771; 1993.

*1* Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoid Receptors and Inhibition of Adenylcyclase"; J. Med. Chem. 1997, 40(20); 3228–3233.

***Rice AS. Cannabinoids and pain. Curr Opin Investig Drugs. Mar. 2001;2(3):399–414.

*1* Richardson JD, Aanonsen I, Hargreaves KM; "Antihyperalgesic effects of a spinal cannabinoids"; Eur. J. Pharmacol. (1998) 346:145–153.

*1* Richardson JD, Kilo S. Hargreaves KM; "Cannabinoids reduce dryperalgesia and inflammation via interaction with peripheral CB1 receptors"; Pain (1998) 75:111–119.

Rinaldi–Carmona et al; "Biochemical and pharmacological characterization of SR141716A, the first potent and selective brain cannabinoid receptor antagonist"; Life Sci.; vol. 56(23/24); 1941–1947 (1995).

Rinaldi–Carmona et al; "SR141716A, a potent and selective antagonist of the brain cannabinoid receptor"; FEBS Lett.; 350; 240–244; (1994).

Santus, Maria; "Studies on thioamides and their derivatives. IX. Synthesis of the derivatives of 1,2,4,5–tetrazine"; Acta Polonae Pharmaceutica; 50(2–3); 183–188; 1993 (abstract only).

Schatz AR et al; "Cannabinoid receptors CB1 and CB2: a characterization of expression and adenylate cyclase modulation within the immune system"; Toxicol Appl Pharmacol. Feb. 1997; 142(2):278–87.

*1* *** Schuel, H., Burkman, L.J., Picone, R.P., Bo, T., Makriyannis, A., Cannabinoid receptors in human sperm. Mol. Biol. Cell., (1997) (8), 325a.

*** Serdarevich B., Caroll K.K., "Synthesis and characterization of 1– and 2–monoglycerides of anteiso fatty acids"; J. Lipid Res.; 7: 277–284; (1966).

Shawali, A.S., Albar, H.A.; "Kinetics and mechanism of dehydrochlorination of N–aryl–C–ethoxycarbonyl formohydrazidoyl chlorides"; Canadian Journal Of Chemistry; 64(5); 871–875; 1986 (abstract only).

*1* *** Shen M. Thayer SA: Cannabinoid receptor agonists protect cultured rat hippocampal neurons from excitotoxicity. Mol. Pharmacol (1996) 54:459–462.

Shim et al; "Three–dimensional quantitative structure–activity relationship study of the cannabimimetic (aminoalkyl)indoles using comparative molecular field analysis"; J. Med. Chem.; 1998, 41(23); 4521–4532; XP–002212407.

Shim et al; "Unified pharmacophoric model for cannabinoids and aminoalkylindoles derived from molecular superimposition of CB1 cannabinoid receptor agonists CP55244 and WIN55212–2"; ACS Symposium series, 1999 719 (rational drug design), 165–184; XP–001095771.

Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989–999; XP–001097918.

*1* *** Simiand J, Keane M, Keane PE, Soubrie P: SR 141716, A CB1 cannabinoid receptor antagonist, selectively reduces sweet food intake in marmoset. Behav. Pharmacol (1998) 9:179–181.

*1* *** Terranova J–P, Storme J–J Lafon N et al; "Improvement of memory in rodents by the selective CB1 cannabinoid receptor antagonist, SR 141716"; Psycho–pharmacol (1996) 126:165–172.

Tius et al; "Conformationally restricted hybrids of CP–55, 940 and HHC: Steroeselective synthesis and activity"; Terahedron; 50 (9); 2671–2680; (1994) (abstract only).

Twitchell, W. et al; "Cannabinoids inhibit N– and P/Q type calcium channels in cultured rat hippocampal neurons"; Journal of Neurophysiology; 78(1); 43–50; 1997 (abstract only).

*** Ueda, N., *Endocannabinoid hydrolases. Prostaglandins & Other Lipid Mediators 2002; 68–69; 521–534.*

*** Vogel Z., Barg J., Levy R., Saya D., Heldman E., Mechoulam R.; *"Anandamide, a brain endogenous compound, interacts specifically with cannabinoid receptors and inhibits adenylate cyclase"; J. Neurochem.; 61(1) 352–355; (1993).*

*1* *** *Wagner JA, Varga K, Jarai Z, Kunos G; 'Mesenteric vasodialtion mediatd by endothelia anandamide receptors'; Hypertension (1999) 33:429–434.*

*1* Watanabe, T.; Miyaura, N.; and Suzuki, A.; "Synthesis of Sterically Hindered Biaryls via the Palladium Catalyzed Cross–Coupling Reaction of Arylboronic Acids or their Esters with Haloarenes"; Synlett 1992, 207–210.

Wiley et al; "Structure activity relationships of indole and pyrrole derived cannabinoids"; J. Pharmacol. Exp. Ther. 1998, 285(3), 995–1004; XP–001097982, Wilson et al; "9–nor–delta8–tetrahydrocannabinol, a cannabinoid of metabolic intersts"; J. Med. Chem.; 17(4); 475–476; (1974).

Wilson et al; "Analgesic properties of the tetrahydrocannabinols, their metabolites and analogs"; J. Med. Chem.; 18(7); 700–703; (1975).

Wilson et al; "9–nor–9–hydrohexahydrocannabinols. Synthesis, some behavioral and analgesic properties, and comparison with the tetrahydrocannabinols"; J. Med. Chem.; 19(9); 1165–1167; (1976).

Yamada et al; "(Aminoalkyl)indole isothiocyanates as potential electrophilic affinity ligands for the brain cannabinoid receptor"; J. Med. Chem. 1996, vol. 39(10), 1967–1974.

Yan, Guo et al; "Synthesis and pharmacological properties of 11–hydroxy–3–(1'–1'– dimethylheptyl)hexahydrocannabionol: a high affinity cannabinoid agonist"; J. Med. Chem.; vol. 37(16); 2619–2622; (1994).

*1* Yan Guo et al; "(–)–11–hydroxy–7'–isothiocyanato–1'–1'dimethylheptyl–delta8–THC: a novel probe for the cannabinoid receptor in the brain"; J. Med. Chem.; 37(23); 3867–3870; (1994).

R =

AM405

AM406

AM410

AM409

AM407

AM408

AM412

AMG3

AMG9

AMG14

SCHEME 1

SCHEME 2.

Scheme 3.

Method I:

ROH is tertiary or secondary alcohols

R =

Method II:

Method III:

Method IV:

Method V:

ROH is tertiary alcohol

ANALGESIC AND IMMUNOMODULATORY CANNABINOIDS

RELATED APPLICATION

The present application is a continuation of U.S. application Ser. No. 09/304,720 filed May 4, 1999; now abandoned, which claims the benefit of U.S. Provisional Application No. 60/084,008, filed May 4, 1998, the contents of each of which are incorporated herein by reference in their entirety.

GOVERNMENT SUPPORT

The invention was supported, in whole or in part, by grants DA3801 and DA9158 from the National Institute of Drug Abuse (NIDA). The Government has certain rights in the invention.

BACKGROUND OF THE INVENTION $\Delta^8$-Tetrahydrocannabinol, the pyschoactive marijuana derived cannabinoid, binds to the CB1 receptor in the brain and to the CB2 receptor in the spleen. Compounds which stimulate the CB1 receptor have been shown to induce analgesia and sedation, to cause mood elevation, to control nausea and appetite and to lower intraocular pressure (Mechoulam, *Cannabinoids as Therapeutic Agents*, CRC Press, Boca Raton, Fla. (1986), Fride and Mechoulam, *Eur. J. Pharmacol.* 231:313 (1993), Crawley et al., *Pharmacol. Biochem. Behav.* 46:967 (1993) and Smith et al., *J. Pharm. Exp. Therap.* 270:219 (1994)). Compounds which stimulate the CB2 receptor have been shown to suppress the immune system (Mechoulam, *Cannabinoids as Therapeutic Agents*, CRC Press, Boca Raton, Fla. (1986), Fride and Mechoulam, *Eur. J. Pharmacol.* 231:313 (1993), Crawley et al., *Pharmacol. Behav.* 46:967 (1993) and Smith et al., *J. Pharm. Exp. Therap.* 270:219 (1994)).

SUMMARY OF THE INVENTION

Disclosed herein is the discovery that cannabinoids with a monocyclic, a fused bicyclic, a bridged bicyclic or a bridged tricyclic side chain at the C-3 position show improved binding affinities for the CB1⁻ and/or CB2 receptor compared with known cannabinoids, which typically have a linear side chain at the C-3 position. For example, the cannabinoids AMG3 and AMG14 have a $K_i$ for the CB1 receptor of less than 1.0 nM and AM731 and AM732 have a $K_i$ for the CB2 receptor of less than 10.0 nM (Example 2). In contrast, the $K_i$ of $\Delta^8$-tetrahydrocannabinol for the CB1 and CB2 receptors is only 45 nM and 14 nM, respectively. The structures of these compounds are shown below.

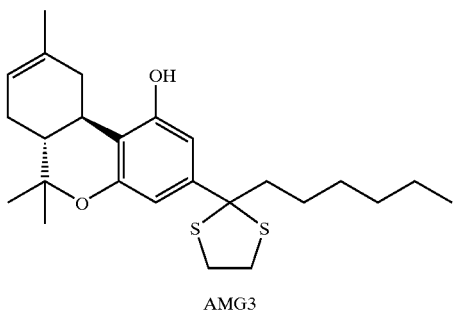

AMG3

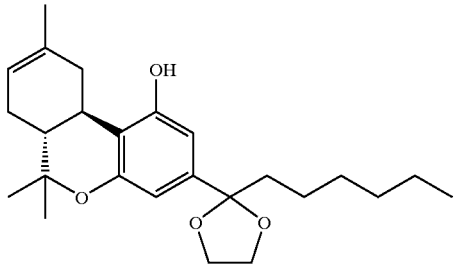

AMG14

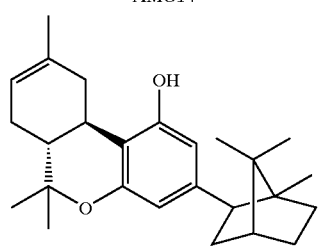

AM731

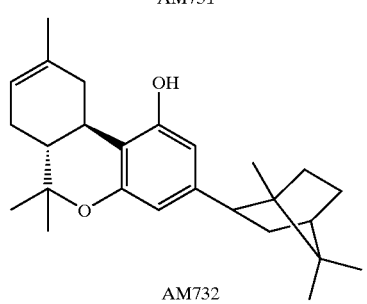

AM732

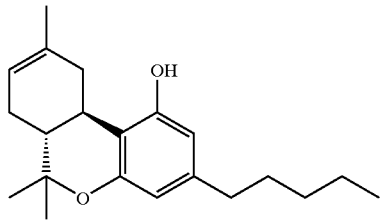

Delta-8-Tetrahydrocannabinol

Based on these results, novel cannabinoids with increased binding affinity for the CB1 and CB2 receptors are disclosed. Also disclosed are methods of stimulating a CB1 and/or CB2 receptor in a subject.

One embodiment of the present invention is a compound represented by Structural Formula (I):

R-X-Y;     (I)

and physiologically acceptable salts thereof.

R is a tricyclic core of a cannabinoid or substituted cannabinoid.

X is covalent bond, —CH— or —CHR$_1$—, wherein R$_1$ is a C1 to C3 substituted or unsubstituted alkyl group.

Y is a heterocyclic ring, a substituted heterocyclic ring, a carbocyclic ring, a substituted carbocyclic ring, a fused bicyclic ring system, a substituted fused bicyclic ring system, a bridged bicyclic ring system, a substituted bridged bicyclic ring system, a bridged tricyclic ring system or a substituted bridged tricyclic ring system.

Another embodiment of the present invention is a method of stimulating a CB1 and/or CB2 receptor in a subject. The method comprises administering to the subject a therapeutically effective amount of a compound represented by Structural Formula (I).

The novel compounds of the present invention can be used to stimulate the CB1 or CB2 receptors in a subject at lower doses and higher selectivity than other known CB1 or CB2 receptor agonists. Thus, they are expected to produce fewer side-effects than known CB1 or CB2 receptor agonists when used for treatment, for example, in treating glaucoma, treating autoimmune disease (e.g., lupus erythematosus, rheumatoid arthritis, psoriasis, multiple sclerosis and inflammatory bowel disease such as ulcerative colitis and Crohn's disease), preventing tissue rejection in organ transplant patients, controlling nausea in patients undergoing chemotherapy and enhancing appetite and controlling pain in individuals with AIDS Wasting Syndrome. In addition, some of these compounds are selective agonists for either the CB1 (e.g., AM411) or CB2 receptor (e.g., AM731 and AM732).

DETAILED DESCRIPTION OF THE INVENTION

Figure 1A:
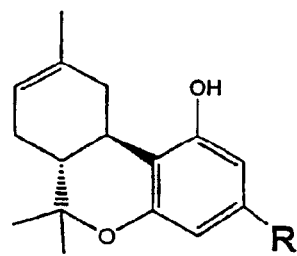
FIGS. 1A, 1B and 1C show the structure of a number of examples of novel compounds included in the present invention.
Figure 1A:
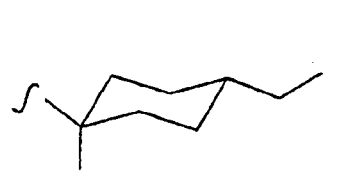
Figure 1A:
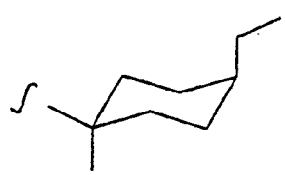
Figure 1A:
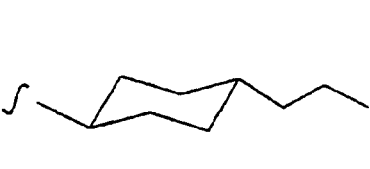
Figure 1A:
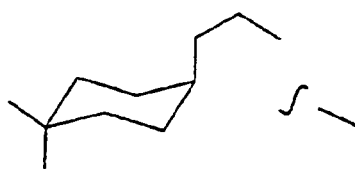
Figure 1A:
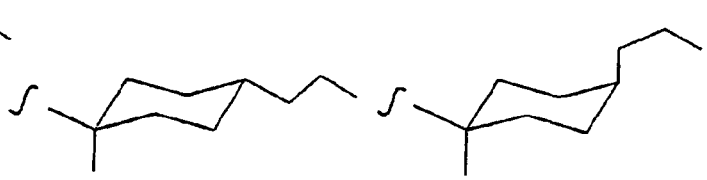
Figure 1A:
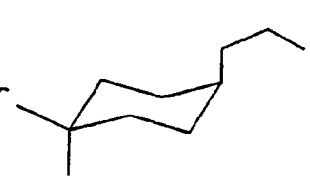
Figure 1B:
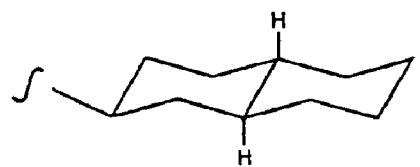
Figure 1B:
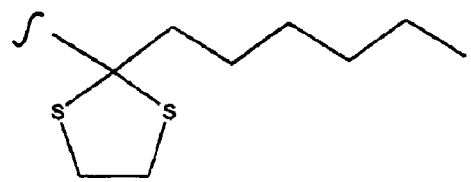
Figure 1B:
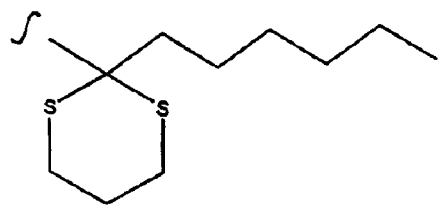
Figure 1B:
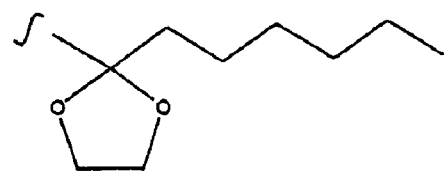
Figure 1C:
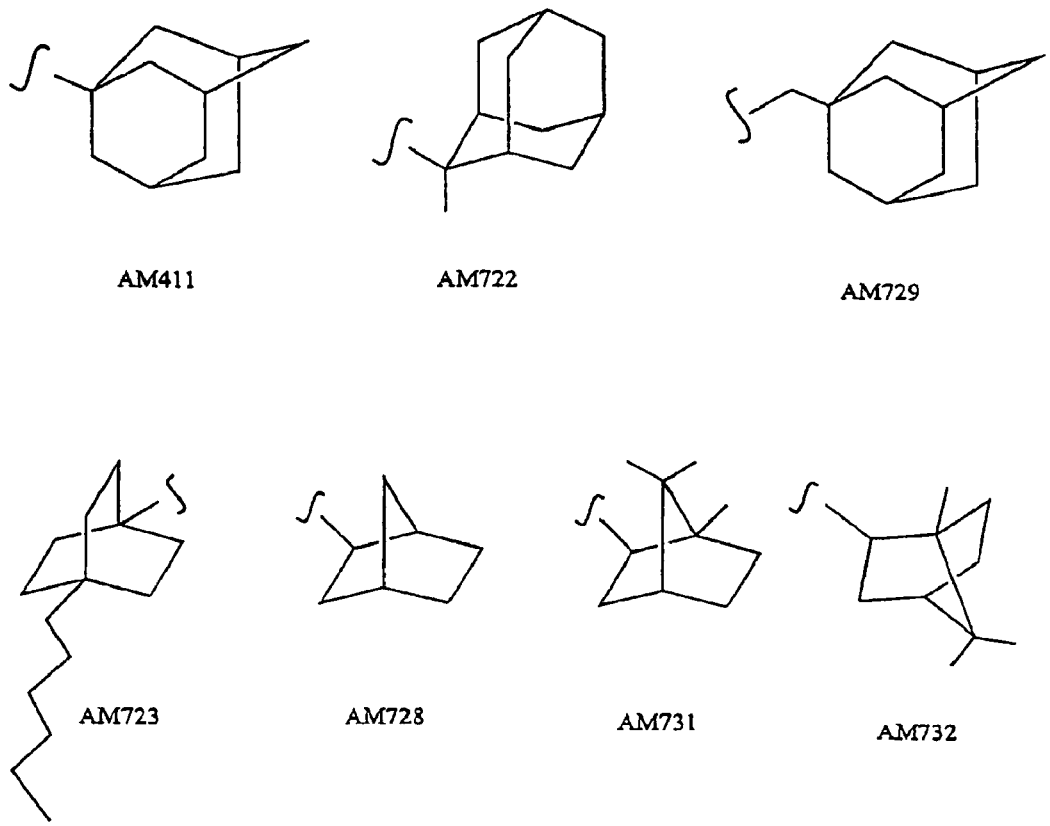

Cannabinoids have a core tricyclic ring system in which a monohydroxylated phenyl ring and a six membered ring are each fused to a central pyran ring or to a central six-membered lactone ring (preferably to a pyran ring). In addition, cannabinoids are able to induce characteristic physiological effects in mammals, including euphoria, delerium, drowsiness, halluncinations, weakness and/or hyporeflexia. The tricyclic core ring system of many cannabinoids is shown in Structural Formula (II). Other cannabinoids have the tricyclic core shown in Structural Formula (II), modified to include one or more double bonds in Ring A, for example, a double bond between carbons 8 and 9, between carbons 9 and 10 or between carbons 9 and 11. Yet other cannabinoids have the core structures described above, modified so that the methyl group bonded to carbon 11 has been replaced, for example, with a hydrogen, hydroxyl, hydroxymethyl, halogen (e.g., chloro, bromo, iodo and fluoro), methoxy, ethoxy, nitrile, nitro, halogenated methyl, halogenated ethyl, methoxymethyl, ethoxymethyl, nitromethyl, ethyl or —CH$_2$CN group. In other cannabinoids, the hydroxyl group at position 1 of the core structure is replaced with —H, —OCH$_3$, —NH$_2$ or —NHCH$_3$. The term "cannabinoid", as it is used herein, also refers to other compounds which: 1) induce one or more of the physiological effects described above which are characteristic of the cannabinoids and 2) have core structures which are related to Structural Formula (II). Also shown in Structural Formula (II) is a numbering system for the atoms in the core tricylic structure.

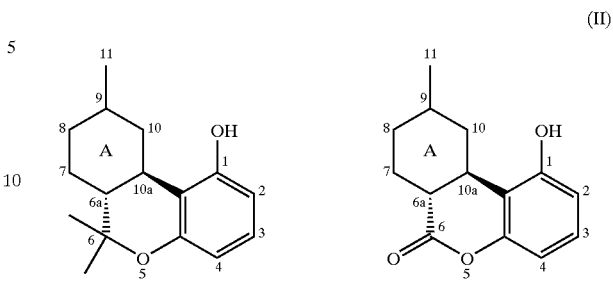

(II)

Cannabinoids also generally have a linear alkyl side chain at position C-3 of the cannabinoid core. In the cannabinoids of the present invention, the linear alkyl side chain is replaced with a heterocyclic ring, a substituted heterocyclic ring, a carbocyclic ring, a substituted carbocyclic ring, a fused bicyclic ring system, a substituted fused bicyclic ring system, a bridged bicyclic ring system, a substituted bridged bicyclic ring system, a bridged tricyclic ring system or a substituted bridged tricyclic ring system.

Suitable substituents for a cannabinoid include groups which do not significantly diminish the ability of a cannabinoid to activate a cannabinoid receptor. Substitutions can occur at positions 2, 4, 6a–10a or at the three methyl groups. Substitutions at more than one position are possible. Substituents which do no significantly diminish the biological activity of cannabinoids are generally small, pharmacophoric groups. Examples include —H, —OH, —OCH$_3$, —OCH$_2$CH$_3$, halogen (e.g., chloro, bromo, iodo and fluoro), —CN, azido, isocyanate, isothiocyanate, —NO$_2$, —CH$_3$, —C(halogen)$_3$, —CH$_2$OH, —CH$_2$OCH$_3$, —CH$_2$OCH$_2$CH$_3$, —CH$_2$(halogen), —CH$_2$CN, —CH$_2$NO$_2$, —CH$_2$CH$_3$, —CH$_2$C(halogen)$_3$, —CH$_2$NH$_2$, —CH$_2$NHCH$_3$ or —CH$_2$N(CH$_3$)$_2$. Suitable substituents can be identified by testing modified cannabinoids in the in vitro CB1 or CB2 assays described in Example 2. Cannabinoids with other substituents can be prepared by modification of the synthetic procedures described in Example 1, e.g., by replacing alcohol (A) in the synthesis shown in FIG. 3 or by replacing the ester/ketone starting material in FIG. 4 with suitably substituted analogs.

Preferably, the tricyclic cannabinoid core is represented by Structural Formula (III):

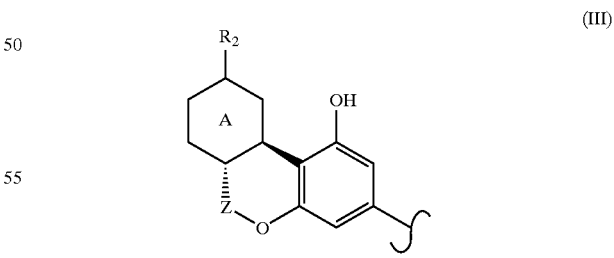

(III)

Ring A has from zero to three endocyclic double bonds. Examples include wherein Ring A is completely saturated, wherein Ring A has three double bonds and wherein Ring A has one endocyclic double bond which connects carbons 9 and 10 or 9 and 11. Preferably, Ring A has one endocyclic double bond wich connects carbons 8 and 9. As used herein, a double bond between two ring atoms is an "endocyclic" double bond.

Z is >C(CH₃)₂ or —C=O. Z is preferably >C(CH₃)₂.

R₂ is —H, —OH, —OCH₃, —OCH₂CH₃, halogen (e.g., chloro, bromo, iodo and fluoro), —CN, —NO₂, —CH₃, —C(halogen)₃, —CH₂OH, —CH₂OCH₃, —CH₂OCH₂CH₃, —CH₂(halogen), —CH₂CN, —CH₂NO₂, —CH₂CH₃, —CH₂C(halogen)₃, —CH₂NH₂, —CH₂NHCH₃ or —CH₂N(CH₃)₂. Preferably, R₂ is —CH₃ or —CH₂OH.

When the tricyclic cannabinoid core is represented by Structural Formula (III), X and Y, taken together, are a C5–C7 carbocyclic ring, a substituted C5–C7 carbocyclic ring, a C5–C7 heterocyclic ring or a C5–C7 substituted heterocyclic ring.

Carbocyclic rings are non-aromatic rings which have only carbon as the ring atoms. Preferably, carbocyclic rings include from about five to about seven ring carbons and are substituted or unsubstituted. Examples include substituted and unsubstituted cyclopentane, cyclopentene, cyclohexane, cyclohexene, cycloheptane and cycloheptene. A preferred example is a substituted cyclohexane shown below in Structural Formula (IV):

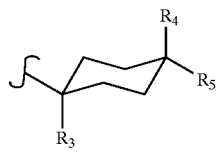

(IV)

R₃ is —H or —CH₃.

R₄ and R₅ are independently —H, a C1–C8 straight chained alkyl group or a C1–C8 substituted straight chained alkyl group. Preferably, at least one of R₄ and R₅ is —H.

Heterocyclic rings are non-aromatic rings with carbon and one or more heteroatoms such oxygen, nitrogen and/or sulfur as ring atoms. Preferably, heterocyclic rings contain from about five to about seven ring atoms and are substituted or unsubstituted. Preferred examples of heterocyclic rings are shown below in Structural Formulas (V) and (VI):

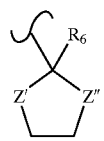

(V)

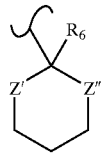

(VI)

Z' and Z'' are independently —S—, —O—, —S(O)— or —N(R₇)—. Preferably, Z' and Z'' are each —O— or —S—.

R₆ is a C1 to about C12 straight chained alkyl or substituted alkyl group. Preferably, R₆ is a C4 to C10 alkyl group.

R₇ is —H or —CH₃.

Other examples of hetetocyclic rings include substituted and unsubstituted 1,3-dioxane, 1,4-dioxane, 1,3-dithiane, 1,4-dithiane, diazetane, tetrahydrofuran, etrahyrothiophene, morpholine, thiomorpholine, pyrrolidine, piperazine, piperidine and thiazolidine.

A fused bicyclic ring comprises two rings which share two ring atoms. Examples include systems such as decalin and tetralin. A preferred example of a fused bicyclic ring system is represented by Structural Formula (VII):

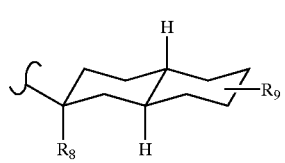

(VII)

R₈ is —H or —CH₃; and

R₉ is —H, a C1–C4 alkyl group or a C1–C4 substituted or unsubstituted alkyl group.

A "bridged bicyclic ring" has two rings in which more than two ring atoms are shared by the two rings. Optionally, a bicyclic ring can have one or more ring heteroatoms such as oxygen, sulfur or nitrogen. A preferred bridged bicyclic ring is a substituted or unsubstituted 2.2.1 seven membered system also referred to as a "norbornyl group". Examples of norbornyl groups are represented by Structural Formula (VIII) and (IX);

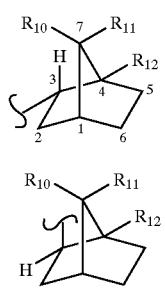

(VIII)

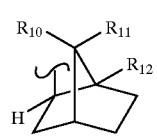

(IX)

R₁₀–R₁₂ are independently —H, C1–C3 alkyl group or C1–C3 substituted alkyl group. Preferably, R₁₀–R₁₂ are independently —H or —CH₃.

Other examples of suitable bridged bicyclic structures include a 3.2.1 eight-membered bicyclic structure, a 3.3.1 nine-membered bicyclic structure and a 2.2.2 eight-membered structure and a 3.3.2 nine-membered structure. The structures of a 3.2.1 eight-membered bicyclic system, a 3.3.1 nine-membered bicyclic system, a 2.2.2 eight-membered bicyclic system and a 3.3.2 nine-membered bicyclic system are provided by Structural Formulas (X)–(XIII):

(X)

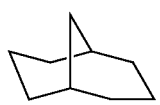

(XI)

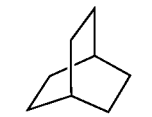

(XII)

(XIII)

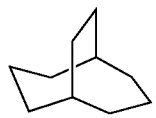

In one example, the bridged bicyclic structures represented by Structural Formulas (X)–(XIII) are substituted by one or more methyl groups.

The nomenclature for bridged bicyclic and tricyclic ring systems indicates the number of ring atoms between bridgeheads. A "bridgehead" is an atom shared by both rings. For example, bicyclo 2.2.1. heptane, shown in Structural Formula (VIII), has two (C-2 and C-3), two (C-5 and C-6) and one (C-7) carbons between the bridgeheads (C-1 and C-4). The numbering scheme for the ring atoms in 2.2.1 heptane is also shown in Structural Formula (VIII).

Bridged tricyclic ring systems comprise three rings, each of which shares two or more ring atoms with each of the other two rings. Optionally, a bridged tricyclic ring can have one or more heteroatoms such as oxygen, nitrogen or sulfur. A preferred example is a substituted or unsubstituted 1,1,1,1,1,1-tricyclic ten-membered ring system, also referred to as an "adamantyl" group. Examples of adamantyl groups are represented by Structural Formula (XIV)–(XVII):

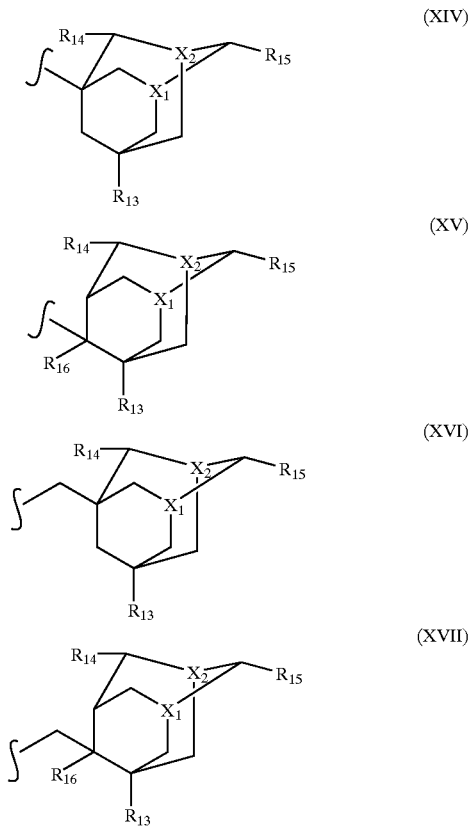

$R_{13}$, $R_{14}$, $R_{15}$ and $R_{16}$ are independently —H, a C1–C3 alkyl group or a C1 to C3 substituted alkyl group. Preferably, $R_{13}$ is —CH$_3$.

$X_1$ and $X_2$ independently are >N— or >CH—. Preferably, $X_1$ and $X_2$ are >CH—.

In another preferred embodiment, the novel cannabinoid analogs of the present invention are represented by Formula (III), modified so that the hydroxyl group attached to the phenyl ring is replaced with an —H and/or modified so that the side chain is attached to position four of the tricyclic cannabinoid core.

Another example of suitable bridged tricyclic system is a substituted or unsubstituted 0,1,1,1,1,1-tricyclic nine-membered ring system.

Suitable substituents for a carbocyclic ring, a heterocyclic ring, a fused bicyclic ring, a bridged bicyclic ring and a bridged tricyclic ring are generally C1–C8 alkyl groups, substituted C1–C8 alkyl groups and small, pharmacophoric groups. Examples of small, pharmacophoric groups include, but are not limited to, —H, —OH, —OCH$_3$, —OCH$_2$CH$_3$, halogen (e.g., chloro, bromo, iodo and fluoro), —CN, azido, isocyanate, isothiocyanate, —NO$_2$, —CH$_3$, —C(halogen)$_3$, —CH$_2$OH, —CH$_2$OCH$_3$, —CH$_2$OCH$_2$CH$_3$, —CH$_2$(halogen), —CH$_2$CN, —CH$_2$NO$_2$, —CH$_2$CH$_3$, —CH$_2$C(halogen)$_3$, —CH$_2$NH$_2$, —CH$_2$NHCH$_3$ or —CH$_2$N(CH$_3$)$_2$. Alkyl groups can be straight chained or branched. Suitable substituents for an alkyl group include small, pharmacophoric groups, as described above.

Figure 2A:
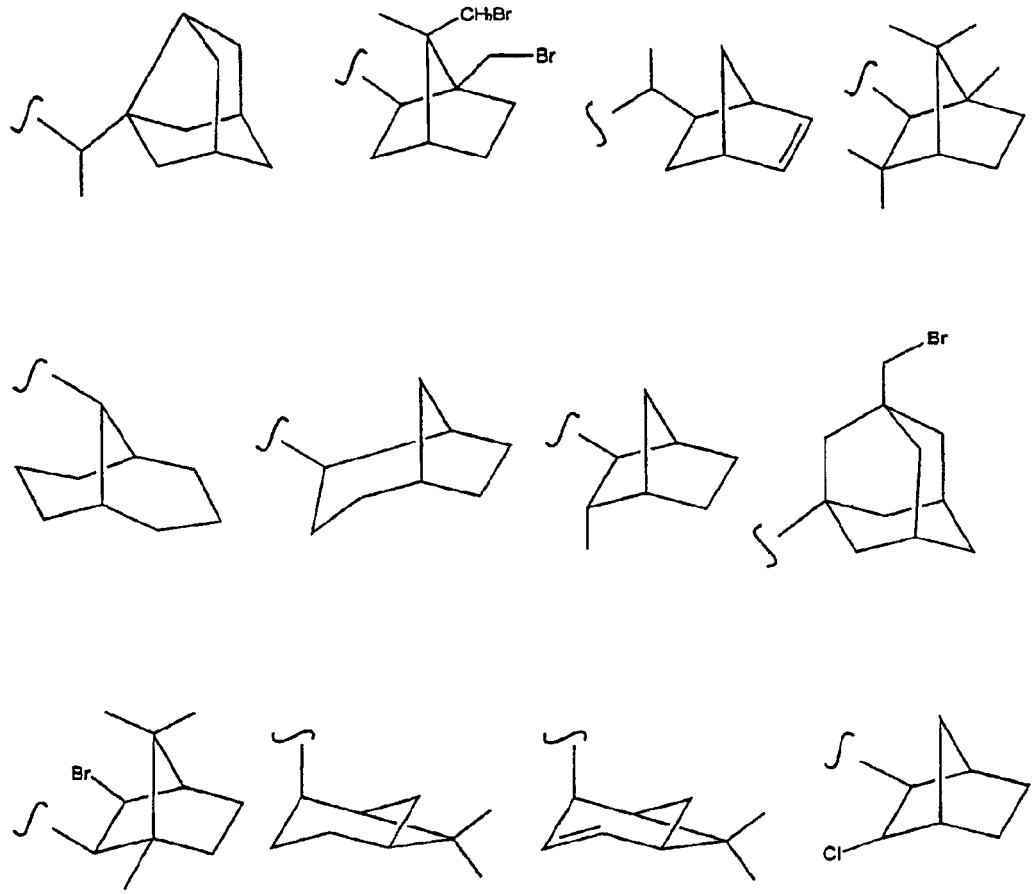
FIGS. 2A and 2B show the structure of a number of novel cannabinoid side chains which can be found in the compounds of the present invention.
Figure 2B:
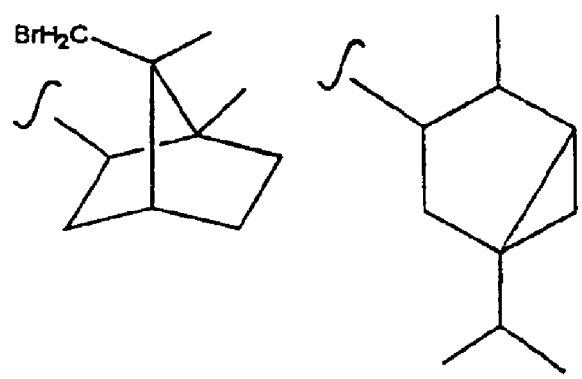

Specific examples of the compounds of the present invention are shown in FIGS. 1 and 2.

In the structural formulas depicted herein, the single or double bond by which a chemical group or moiety is connected to the remainder of the molecule or compound is indicated by the following symbol:

For example, the corresponding symbol in Structural Formula (VIII) indicates that the norbornyl group, which is represented in Structural Formula (I) by Y, is connected to R or X in Structural Formula (I) by a single covalent bond with between carbon three of the norbornyl group and R or X.

A "therapeutically effective amount" is the quantity of compound which results in a desired therapeutic effect in a subject, e.g., immune system suppression, decreased nausea in patients undergoing chemotherapy, increased appetite and/or decreased pain in individuals with AIDS Wasting Syndrome or intraocular pressure in individuals with glaucoma. The specific dosage level of active ingredient will depend upon a number of factors, including, for example, biological activity of the particular preparation, age, body weight, sex and general health of the subject being treated. Typically, a "therapeutically effective amount" of the compound ranges from about 10 mg/day to about 1000 mg/day, preferably from about 50 mg/day to about 500 mg/day.

As used herein, a "subject" refers to a human. An "animal" refers to veterinary animals, such as dogs, cats, horses, and the like, and farm animals, such as cows, pigs, guinea pigs and the like.

The compounds of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to capsular and tablet formulations (for oral and rectal administration), liquid formulations (for oral, intravenous, intramuscular or subcutaneous administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles may include saline, sterile water, Ringer's solution, and isotonic sodium chloride solutions.

Figure 3:
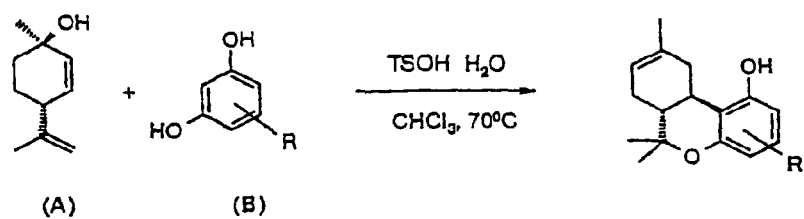
FIG. 3 is a schematic showing a general procedure for the preparation of $\Delta^8$-tetrahydrocannabinol analogs and 2- and 4-substituted deoxy-$\Delta^8$-tetrahydrocannabinols.
Figure 3:
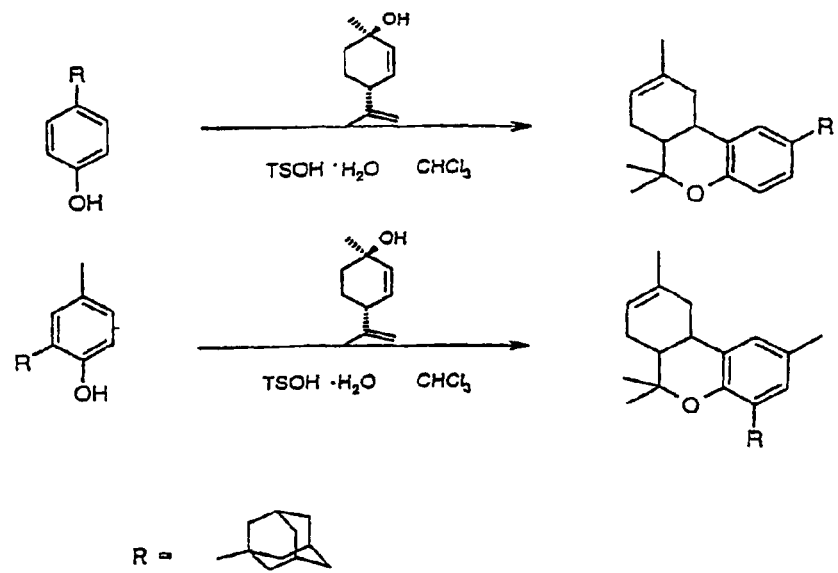
Figure 4:
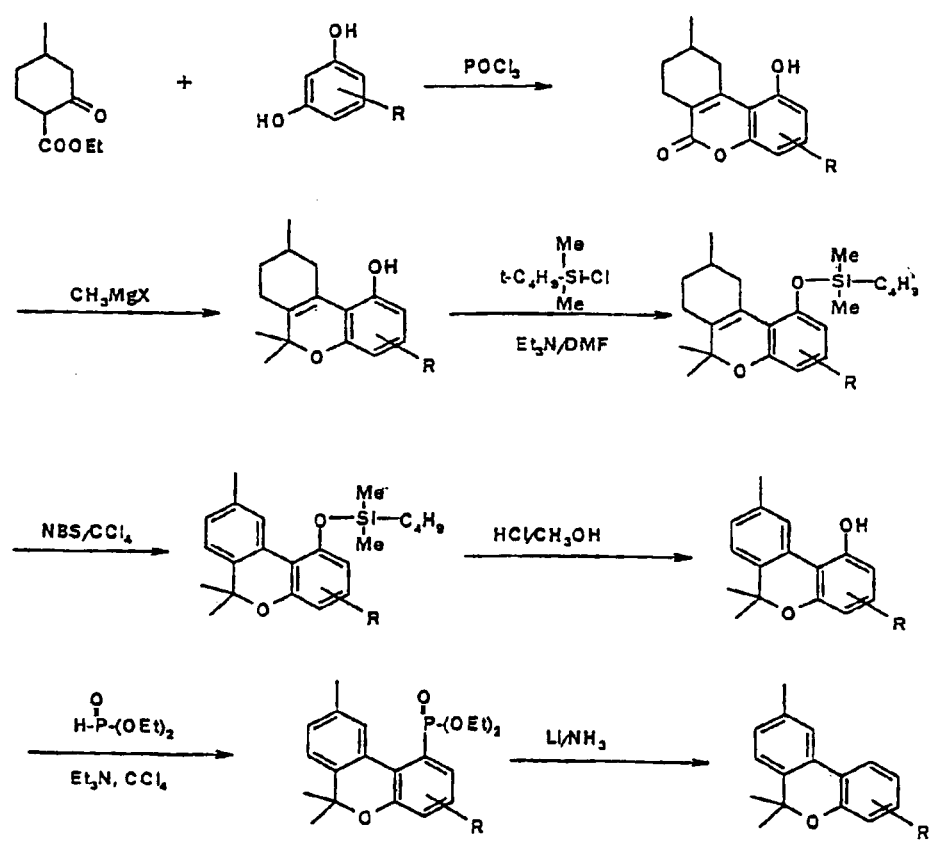
FIG. 4 is a schematic of the synthesis of cannabinol analogs with noncyclic side chains.
Figure 5A:
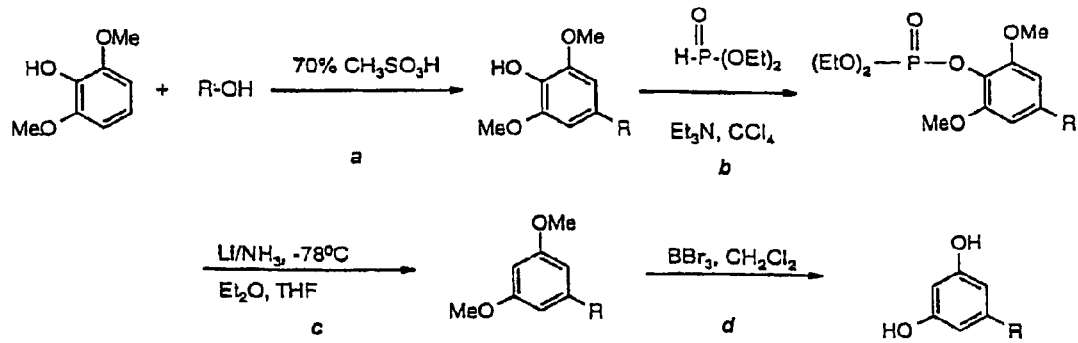
FIGS. 5A and 5B are schematics showing the preparation of the rescorinol starting materials used in the syntheses shown in FIGS. 3 and 4.
Figure 5A:
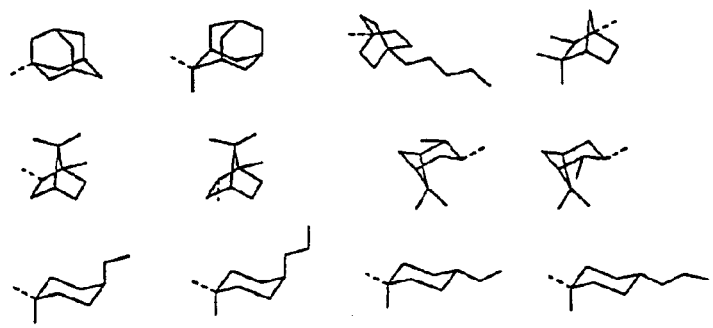
Figure 5A:
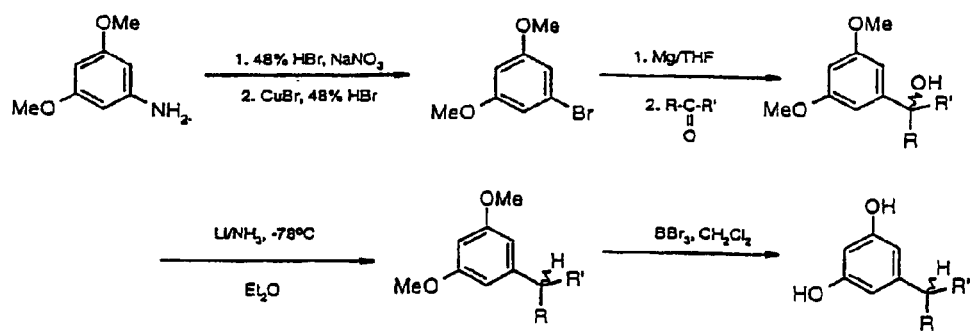
Figure 5A:
Figure 5B:
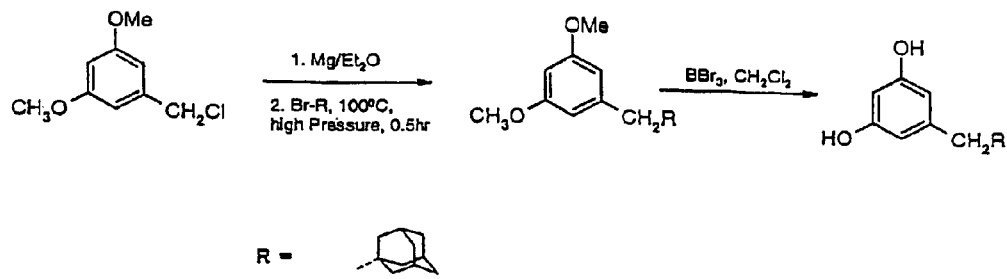
Figure 5B:
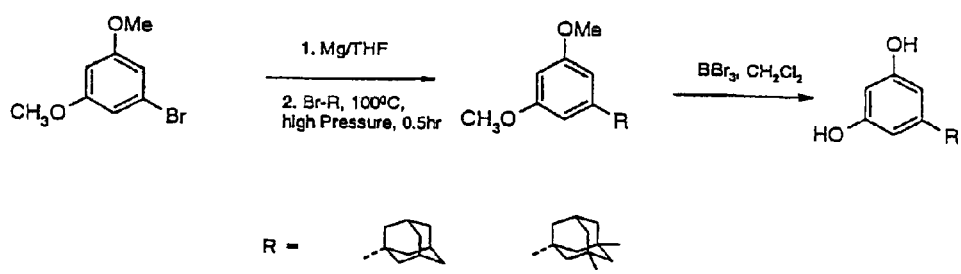
Figure 5B:
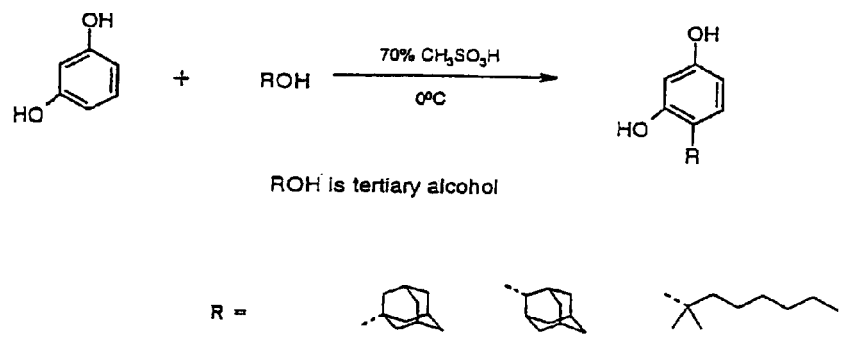

The compounds of the present invention can be prepared by the syntheses shown in FIGS. 3–5. Specific conditions for reactions shown in FIGS. 3–5 are provided in Example 1.

Also included in the present invention are physiologically acceptable salts of the novel compounds disclosed herein. Salts of compounds containing a phenolic group or other acidic functional group can be prepared by reacting with a suitable base, for example, a hydroxide base or amine base. Salts of acidic functional groups contain a countercation such as sodium, potassium, ammonium and the like. Salts of compounds containing an amine or other basic group can be obtained, for example, by reacting with a suitable organic or inorganic acid, such as hydrogen chloride, hydrogen bromide, acetic acid, perchloric acid and the like. Compounds with quaternary ammonium group also contain a counteranion such as chloride, bromide, iodide, acetate, perchlorate and the like.

The novel compounds of the present invention have utilities other than immunomodulation. For example, the disclosed cannabinoids can be used to screen for cells which express cannabinoid receptors (CB1 or CB2). The cells are contacted with a radiolabelled cannabinoid, washed to remove unbound compound and then counted to assess retained radioactivity. Cells which retain radioactivity bind cannabinoids and are there likely to express a cannabinoid receptor. Preferably, the cannabinoid is a CB1 or CB2 selective cannabinoid and therefore identifies cells which express the CB1 or CB2 receptor, respetively.

The disclosed cannabinoids can also be used to identify other compounds which bind to a cannabinoid receptor. For example, radiolabelled cannabinoids can be used in place of CP-55,940 in the CB1 or CB2 assay described in Example 1. Radiolabeled cannabinoids can be prepared by, for example, by reducing the ketones used in Method II of FIG. 5 with a suitable radiolabeled reducing agent such a tritiated sodium borohydride and oxidizing back to the ketone with a suitable oxidizing agent such as pyridinium chloro chromate (PCC). Preferably, the cannabinoid is selective for the CB1 or CB2 receptor.

The invention is illustrated by the following examples which are not intended to be limiting in any way.

EXEMPLIFICATION

Example 1

Preparation of the Compound of the Present Invention

Resorcinol Synthesis (I). Resorcinols Synthesized by Method I in FIG. 5

A procedure for preparing resorcinols is described in Dominiami, et al., *J. Org. Chem.* 42:344 (1977). The crude resorcinols obtained by this method were purified by silica gel column chromatography eluted with a 2:1 mixture of petroleum ether and acetone.

(II). Resorcinols Synthesized by Method II

Preparation of 5-Bromo-3,5-Dimethoxy Benzene. 100 mmol of 3,5-dimethoxyaniline were mixed with 75 ml of 48% hydrobromic acid. 150 mmol of sodium nitrite powder were added portionally over 20 minutes with rigorous stirring. The reaction was monitored by iodine-starch test paper until the paper turned blue. The resulting diazonium salt solution was added to a pre-prepared boiling solution of 50 mmol copper (I) bromide in 7 ml of 48% hydrobromic acid. The addition was complete after 20 minutes. The reaction mixture was then heated for 30 minutes with rigorous stirring. Steam distillation of the reaction mixture provided a white solid product with a yield of 40%.

Preparation of 1'-hydroxy-1-alkyl-3,5-dimethoxybenzene. 1 mmol of 3,5-dimethoxyphenylmagnesium bromide was prepared in 8 ml of anhydrous THF according to procedures disclosed in Harvill and Herbst, *J. Org. Chem.*, 9:21 (1944), the entire teachings of which are incorporated herein by reference. A solution of 1.1 mmol of a suitable ketone in 2 ml of anhydrous THF was added dropwise to the Grignard reagent solution. The mixture was refluxed for 2 to 3 hours and then quenched with the addition of saturated ammonium chloride solution. After work up and purification by column chromatography, product was collected in a yield of 95%.

Preparation of 1-alkyl-3,5-dimethoxybenzene. This compound was synthesized through lithium ammonia reduction of 1'-hydroxy-1-alkyl-3,5-dimethoxybenzene by the method described in Gray et al., *J. Org. Chem.*, Vol.40:3151 (1975), the entire teachings of which are incorporated herein by reference.

Preparation of 5-alkyl-resorcinol. This resorcinol was perpetrated by demethylation of 1-alkyl-3,5-dimethoxybenzene through the method described in Dominiami, et al., *J. Org. Chem.* 42:344 (1977), the entire teachings of which are incorporated herein by reference.

(III) Resorcinols Synthesized by Method III in FIG. 5

Preparation of 1-alkyl-3,5-dimethoxybenzene. A ethereal 10 mmol of 3,5-dimethoxybenzylmagnesium bromide was prepared in the usual manner with 40 ml of anhydrous ether according to procedures disclosed in Harvill and Herbst, *J. Org. Chem.*, 9:21 (1944). The solution of Grignard reagent was concentrated to 15 ml and transferred into an Ace pressure tube containing a 10 ml ethereal solution of 10 mmol of a suitable tertiary alkyl bromide. The mixture was sealed and heated in a 100° C. oil bath with stirring for 30 minutes, as described in Osama, et al., *J. Org. Chem.*, 36:205 (1971), Ohno, et al., *J. Org. Chem.*, 53:729 (1988) and Love, et al., *J. Med. Chem.*, 16:1200 (1973), the entire teachings of which are incorporated herein by reference. The crude product was purified through column chromatoghraphy with a yield about 25%.

Preparation of 5-alkyl-resorcinol. This resorcinol was prepared by demethylation of 1-alkyl-3,5-dimethoxybenzene by methods described in Dominiami, et al., *J. Org. Chem.*, 42:344 (1977), the entire teachings of which are incorporated herein by reference.

(IV). Resorcinols Synthesized by Method IV in FIG. 5

The procedure for the preparation of these resorcinols is the same as described in (III), except that the Grignard reagent was prepared using tetrahydrofuran.

(V). Resorcinols Synthesized by Method V in FIG. 5

A mixture of 100 mmol resorcinol and 100 mmol tertiary alcohol in 200 ml of 70% methanesulfonic acid was stirred at 0° C. for 12 hours for the preparation of linear side chain resorcinols, and stirred for 3 to 4 hours at room temperature for preparation of cyclic side chain resorcinols. The reaction was quenched by addition of an excess of water. The crude product was purified by column chromatography. The column was eluted with 2:1 mixture of petroleum ether and acetone. Yield was about 70%.

Synthesis of $\Delta^8$-Tetrahydrocannabinol Analogs Via the Method of Scheme 1 of FIG. 3.

A mixture of 1 mmol of the resorcinol, 1 mmol trans-p-mentha-2, 8-dien-1-ol and 18 mg of p-toluenesulfonic acid monohydrate in 10 ml of chloroform was stirred and heated in a 70° C. oil bath for 2 to 4 hours. Then the reaction temperature was lowered to room temperature and quenched by addition of 5 ml of saturated sodium bicarbonate solution. After separation, the aqueous layer was extracted twice with methylene chloride. The combined organic layer was washed with brine and dried over sodium sulfate. Removal of solvent by vacuum evaporation provides a yellow oil crude product. The product was purified by column chromatography. By eluting with 20:1 mixture of petroleum ether and ethyl acetate. The yield was generally about 65%. For some stereoisomers, HPLC purification was performed with a chiral column. The mobil phase was a mixture of hexane and isopropanol.

Synthesis of 1-Deoxy-$\Delta^8$-Tetrahydrocannabinol Via the Method of Scheme 2 in FIG. 3

A mixture of 1 mmol of the phenol, 3 mmol trans-p-mentha-2, 8-dien-1-01 and 35 mg of p-toluenesulfonic acid monohydrate in 10 ml of chloroform was stirred and heated in a 70° C. oil bath for 4 to 8 hours. Then the reaction temperature was lowered to room temperature. The reaction was quenched by addition of 5 ml of saturated sodium bicarbonate solution. After separation, the aqueous layer was extracted twice by methylene chloride. The combined organic layer was washed by brine and dried over sodium sulfate. Removal of solvent by vacuum evaporation provided a yellow oil crude product. The product was purified by column chromatography, eluting with 20:1 mixture of petroleum ether and ethyl acetate. The yield was generally about 15% to 20%.

Synthesis of Cannabinol and 1-Deoxy-Cannabinol Analogs Via the Method of Scheme 3 of FIG. 4

The experimental procedures are as described in Love, et al., *J. Med. Chem.*, 16:1200 (1973), Meltzer, et al., Synthsis, 1981, 985, and Gareau, et al., *Bioorg. Med. Chem. Lett.*, 6:189 (1996), the entire teachings of which are incorporated herein by reference.

Example 2

Compounds of the Present Invention Bind to the CB1 and/or CB2 Receptor

Radioligand Binding Assay

The binding affinities of the novel compounds described in this invention for the central cannabinoid receptor was assessed using rat forebrain membranes as a source of CB1. Membranes were prepared as described by the method of Dodd et al., *Brain Res.* 226:107 (1981), the entire teachings of which are incorporated herein by reference. Rat whole brains minus the cerebral cortex were diced with a razor blade and homogenized in 0.32 M sucrose, pH 7.4. The resulting suspension was spun at 400×g at 4° C. The supernatant was decanted and layered over 1.2 M sucrose in TME buffer (25 mM Tris base, 5 mM MgCl$_2$ 1 mMEDTA, pH 7.4) and spun at 109,000×g. The interface containing plasma membrane protein was collected, pooled and layered over 0.8 M sucrose in TME, pH 7.4. The pellet was carefully resuspended in TME, pH 7.4 and the total protein content was assayed by the method of Markwell et al., *Anal. Biochem.* 87:206 (1978), the entire teachings of which are incorporated herein by reference. Protein was aliquotted, frozen under liquid nitrogen and stored at −80° C. until use.

Approximately 30 μg of tissue was incubated in silanized 96 well microtiter plate with TME containing 0.1% essentially fatty acid free bovine serum albumin (BSA), 0.8 nM [H$^3$]CP-55,940 and various concentrations of the test compound in a final volume of 200 μL. Assays were incubated at 30° C. for 1 hour. The samples were filtered using Packard Filtermate 196 and Whatman GF/C Filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Non-specific binding was assessed using 100 nM CP-55,940. Data collected from three independent experiments performed with duplicate determinations were normalized between 100% and 0% specific binding for [H$^3$]CP-55,940, determined using buffer and 100 nM CP-55,940. The normalized data was analyzed using a 4 parameter nonlinear logistic equation to yield IC$_{50}$ values. Data from at least two independent experiments performed in duplicate were used to calculate IC$_{50}$ values which were convered to K$_i$ values using the assumptions of Cheng and Prusoff, *Biochem. Pharmacol.*, 22:3099 (1973), the entire teachings of which are incorporated herein by reference.

Mouse spleen was used a source of CB2 receptors to assess binding affinity of analogs described in this invention. The CB2 binding assay was conducted in the same manner as for CB1. Silanized centrifuge tubes were used throughout to minimize receptor loss due to adsorption.

The K$_i$s (nanomolar) for a number of the compounds of the present invention are shown in the Table below:

TABLE

| Compound | K$_1$ in nM for the CB1 Receptor | K$_1$ in nM for the CB2 Receptor |
| --- | --- | --- |
| AM405 | 19.1 | |
| AM406 | 14.5 | |
| AM410 | 25.8 | 22.3 |
| AM409 | 75.3 | |
| AN407 | 9.1 | |
| AM408 | 18.3 | |
| AM412 | 182.9 | 85.0 |
| AMG3 | 0.32 | 1.7 |
| AMG9 | 3.6 | |
| AMG14 | 0.2 | |
| AM411 | 6.9 | 52.0 |
| AM722 | 78.2 | 40.3 |
| AM729 | 29.3 | 26.9 |
| AM723 | 382.6 | 2845.0 |
| AM728 | 30.7 | 32.8 |
| AN731 | 60.6 | 6.1 |
| AM732 | 20.1 | 2.0 |

While this invention has been particularly shown and described with references to preferred embodiments thereof, it will be understood by those skilled in the art that various changes in form and details may be made therein without departing from the spirit and scope of the invention as defined by the appended claims.

What is claimed is:
1. A compound represented by the following structural formula:

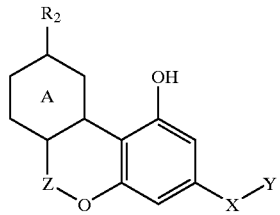

and physiologically acceptable salts thereof, wherein:
ring A has zero to three endocyclic double bonds;
Z is >C(CH$_3$)$_2$ or —C═O;
R$_2$ is —H, —OH, —OCH$_3$, —OCH$_2$CH$_3$, halogen, —CN, —NO$_2$, —CH$_3$, —C(halogen)$_3$, —CH$_2$OH, —CH$_2$OCH$_3$, —CH$_2$OCH$_2$CH$_3$, —CH$_2$(halogen), —CH$_2$CN, —CH$_2$NO$_2$, —CH$_2$CH$_3$, —CH$_2$C(halogen)$_3$, —CH$_2$NH$_2$, —CH$_2$NHCH$_3$ or —CH$_2$N(CH$_3$)$_2$;

X is a covalent bond; and

Y is a fused bicyclic ring system having only carbon atoms as ring members, a substituted fused bicyclic ring system having only carbon atoms as ring members, a bridged bicyclic ring system having only carbon atoms as ring members, a substituted bridged bicyclic ring system having only carbon atoms as ring members, a bridged tricyclic ring system or a substituted bridged tricyclic ring system.

2. The compound of claim 1 wherein:

X is a covalent bond; and

Y is a fused bicyclic ring system or a substituted fused bicyclic ring system.

3. The compound of claim 1 wherein:

X is a covalent bond; and

Y is represented by the following structural formula:

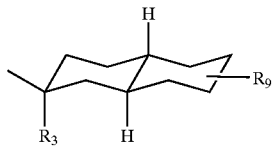

wherein R$_8$ is H or CH$_3$; and

R$_9$ is H, a C1 to C4 alkyl group or a substituted C1 to C4 alkyl group.

4. The compound of claim 1 wherein:

X is a covalent bond; and

Y is a bridged bicyclic ring system, a substituted bridged bicyclic ring system, a bridged tricyclic ring system or a substituted bridged tricyclic ring system.

5. The compound of claim 1 wherein:

X is a covalent bond; and

Y is a substituted or unsubstituted 0,1,1,1,1,1-tricyclic nine-membered ring system, a substituted or unsubstituted 1,3,3-bicyclic nine-membered ring system, a substituted or unsubstituted 1,2,3-bicyclic eight-membered ring system, a substituted or unsubstituted 1,1,1,1,1,1-tricyclic ten-membered ring system, a substituted or unsubstituted 1,1,3-bicyclic nine-membered ring system or a substituted or unsubstituted 1,3-bicyclic six-membered ring system.

6. The compound of claim 1 wherein:

X is a covalent bond; and

Y is a substituted or unsubstituted norbornyl ring system.

7. The compound of claim 1 wherein:

X is a covalent bond; and

Y is a substituted or unsubstituted norbornyl ring system represented by the following formula:

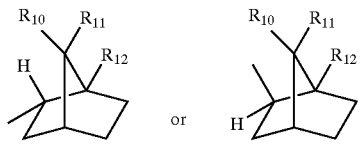

wherein R$_{10}$, R$_{11}$, and R$_{12}$ are each independently selected from H, a C1 to C3 alkyl group or a substituted C1 to C3 alkyl group.

8. The compound of claim 7 wherein R$_{10}$, R$_{11}$ and R$_{12}$ are each independently selected from H or CH$_3$.

9. The compound of claim 1 wherein:

X is a covalent bond; and

Y is a substituted or unsubstituted adamantyl ring system.

10. The compound of claim 1 wherein:

X is a covalent bond; and

Y is represented by the following structural formula:

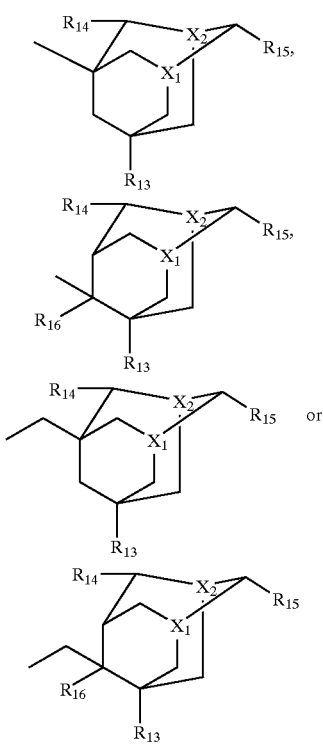

wherein:

R$_{13}$, R$_{14}$, R$_{15}$ and R$_{16}$ are each independently selected from H, a C1 to C3 alkyl group or a C1 to C3 substituted alkyl group; and X$_1$ and X$_2$ are each >CH—.

11. The compound of claim 10 wherein R$_{13}$ is CH$_3$; R$_{14}$, R$_{15}$ and R$_{16}$ are each H; and X$_1$ and X$_2$ are each >CH—.

12. The compound of claim 1 wherein:

X is a covalent bond; and

Y is represented by the following structural formula:

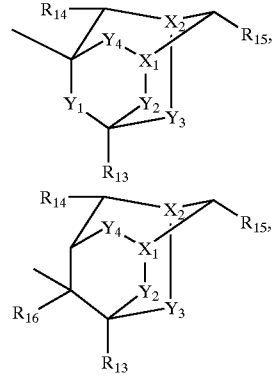

-continued
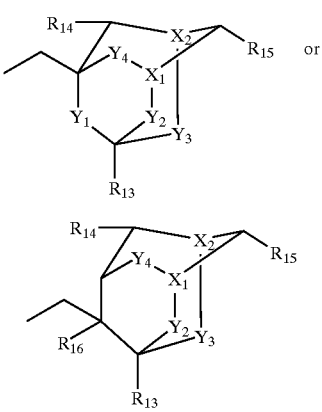
wherein:
$R_{13}$, $R_{14}$, $R_{15}$ and $R_{16}$ are each independently selected from H, a C1 to C3 alkyl group or a C1 to C3 substituted alkyl group;
$X_1$, $X_2$ and $X_3$ are each >CH—; and
$Y_1$, $Y_2$, $Y_3$ and $Y_4$ are each >CH$_2$.
13. The compound of claim 1 represented by the following structural formula:
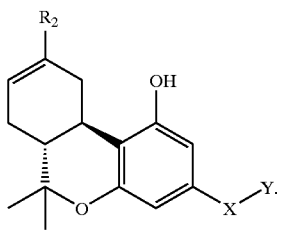
14. The compound of claim 1 represented by the following structural formula:
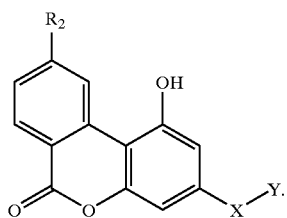
* * * * *

UNITED STATES PATENT AND TRADEMARK OFFICE
CERTIFICATE OF CORRECTION

PATENT NO. : 6,939,977 B2  
APPLICATION NO. : 10/309686  
DATED : September 6, 2005  
INVENTOR(S) : Makriyannis et al.

Page 1 of 1

It is certified that error appears in the above-identified patent and that said Letters Patent is hereby corrected as shown below:

Column 13:  
Line 12, after "system" insert --having only carbon atoms as ring members--.

Line 28, delete "$R_3$" and insert --$R_8$--.

Column 15:  
Lines 1 – 19 delete:                    and insert:

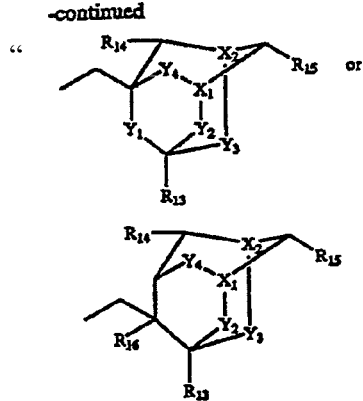

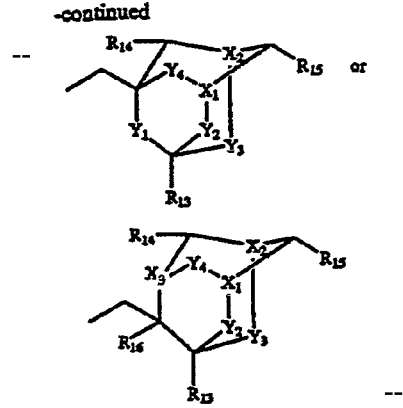

Signed and Sealed this

Seventh Day of November, 2006

JON W. DUDAS  
*Director of the United States Patent and Trademark Office*